United States Patent [19]

Shirahata et al.

[11] Patent Number: 5,114,916
[45] Date of Patent: May 19, 1992

[54] THERAPEUTIC AGENT FOR THE PREVENTION OF INTRAVENTRICULAR HEMORRHAGE IN PREMATURE INFANTS

[75] Inventors: Akira Shirahata, Fukuoka; Minoru Uchida, Kanagawa; Satoshi Tanaka; Kenichiro Tsumura, both of Chiba, all of Japan

[73] Assignee: Hoechst Japan Limited, Tokyo, Japan

[21] Appl. No.: 480,358

[22] Filed: Feb. 14, 1990

Related U.S. Application Data

[63] Continuation of Ser. No. 313,568, Feb. 22, 1989, abandoned.

[30] Foreign Application Priority Data

Feb. 24, 1988 [JP] Japan .................................. 63-39646

[51] Int. Cl.$^5$ .............................................. A61K 37/00
[52] U.S. Cl. ......................................... 514/2; 514/802
[58] Field of Search ..................................... 514/2, 802

[56] References Cited

U.S. PATENT DOCUMENTS 3,717,708  2/1973  Wada et al. ......................... 514/802

FOREIGN PATENT DOCUMENTS 3622642  1/1988  Fed. Rep. of Germany .

*Primary Examiner*—S. J. Friedman
*Attorney, Agent, or Firm*—Finnegan, Henderson, Farabow, Garrett and Dunner

[57] ABSTRACT

Human blood coagulation factor XIII allows the prevention of intraventricular hemorrhage when administered to premature infants, preferably by intravenous injections.

5 Claims, No Drawings

THERAPEUTIC AGENT FOR THE PREVENTION OF INTRAVENTRICULAR HEMORRHAGE IN PREMATURE INFANTS

This application is a continuation-in-part of application Ser. No. 07/313,568, filed Feb. 22, 1989 now abandoned.

DETAILED DESCRIPTION OF THE INVENTION

1. Field of the Invention

The present invention relates to a therapeutic agent for the prevention of intraventricular hemorrhage in premature infants.

2. Prior Art

Intraventricular hemorrhage of newborn infants is one of the diseases resulting in a very high mortality rate. It is said that the frequency of peripheral ventricular hemorrhage or intraventricular hemorrhage in premature infants or infants with severe asphyxia is around from 40 to 60 percent, whereas traumatic hemorrhage of infants has been greatly decreased with the remarkable progress in neonatology in recent years.

Though the cause of intraventricular hemorrhage has not completely been elucidated, it is thought to originate in the prematurity of the capillary vessel system and its surrounding tissue of the ventricular subependymal germinal matrix remaining in the infant brain as well as in other triggering causes such as a traumatic wound, anoxemia and a high $CO_2$ level in blood which may have occurred at the time of delivery.

There are no effective therapies which can prevent this type of hemorrhage. The subsequent enlargement of ventricularis and other effects become a significant obstacle to the growth of the babies. Therefore, prevention of hemorrhage is very important.

Recently several substances such as phenobarbital, ethamsylate, vitamin E, indomethacin and frozen fresh plasma were experimentarily administered for the prevention of peripheral ventricular and intraventricular hemorrhage but their effectiveness was still unclear. It was said that they did not change at all the frequency of severe hemorrhage.

PROBLEM TO BE SOLVED BY THE INVENTION

None of the existing therapeutic methods are able to prevent the disease effectively and, therefore, the frequency of the disease has been almost constant for 10 years. The object of this invention is to provide a therapeutic agent for preventing the disease especially in cases with high frequency.

Measures to solve the problems

This invention relates to a pharmaceutical composition for the prevention of intraventricular hemorrhage in premature infants, which contains human blood coagulation factor XIII (hereinafter referred to as factor XIII) as the active ingredient.

Factor XIII preparations have been used mainly to treat wound healing disturbances. We have found factor XIII to prevent intraventricular hemorrhage in premature infants. This finding has led us to accomplish the invention.

The existence of factor XIII was first suggested by Robbins in 1944. In the early days it had also been called fibrin-stabilizing factor, fibrinase or plasma transglutaminase, but, after studies by Laki and Lorand et al., factor XIII was adopted as its official name at the Congress of the International Society on Thrombosis and Haemostasis in 1963. It is commonly seen in the plasma, placenta, etc. It acts as a transaminase that is activated by thrombin and $Ca^{2+}$ and forms cross-links between fibrin molecules. Those cross-links grow into a strong fibrin network that is stable against physical shocks and chemical stimuli. Besides this fibrin-stabilizing effect, factor XIII has also been demonstrated to play an important role in the wound healing process: that is, it forms cross-links between fibrin and fibronectin molecules and promotes fibroblast proliferation and epidermis formation. Factor XIII preparations have already been in wide use as a therapeutic agent for wound healing disturbances, etc. The number of domestic and overseas patients treated with them has exceeded 10,000. This accumulation of clinical experience ensures that they are totally free from side effects and toxicity as long as they are used at a usual dose of 20 to 50 units/kg body weight.

The following are the detailed results of clinical trials that clearly demonstrate the effectiveness of factor XIII in the prevention of intraventricular hemorrhage in premature infants:

Patients

Twenty four of 48 newborn infants, who were born from January 1986 to October 1987 and fell into one of the categories (1) and (2), were randomly selected at a hospital and treated with factor XIII concentration.

(1) who were artificially respirated and whose gestational age or birth weight is less than 37 weeks or 2000 g.

(2) who were not artificially respirated and whose gestational age or birth weight is less than 33 weeks or 1500 g.

Method of treatment 70-100 units/body/day of F XIII were administered by intravenous injection for 3 days within 6 hours after delivery.

Result

There was no significant difference in respect to the back ground between the two groups, treated group and control group, which proved a good randomization.

Risk factors of intraventricular hemorrhage shown in Table 1 were taken into account.

TABLE 1

Scoring system of risk factors for intraventricular hemorrhage in newborn infants

| Items | 0 | 1 | 2 |
|---|---|---|---|
| gestational age (weeks) | $\geq 34$ | $\geq 29, <34$ | $<29$ |
| birth weight (grams) | $\geq 1000$ | $\geq 600, <1000$ | $<600$ |
| apgar score (5 min.) | $\geq 7$ | $\geq 4, \leq 6$ | $\leq 3$ |
| peak inspiratory pressure (torr) | $\leq 10$ | $>10, \leq 25$ | $>25$ |
| pH of arterial gas | $\geq 7.25$ | $<7.25 \geq 7.10$ | $<7.10$ |
| $PaCO_2$ (torr) | $\leq 55$ | $>55, \leq 80$ | $>80$ |
| air leak | absent | | present |
| patent ductus arteriosus | absent | | present |
| intrapulmonary and/or intrathoracic hemorrhage | absent | | present |
| intestinal and/or intraabdominal hemorrhage | absent | | present |
| platelet counts ($\times 10^4/\mu l$) | $\geq 15$ | $\geq 10, <15$ | $<10$ |
| plasma fibrinogen (mg/dl) | $\geq 150$ | $\geq 100, <150$ | $<100$ |
| serum fibrin degradation | | | |

TABLE 1-continued

Scoring system of risk factors for intraventricular hemorrhage in newborn infants

| Items | 0 | 1 | 2 |
|---|---|---|---|
| products (μg/ml) | <10 | ≧10, <40 | ≧40 |

Taking account of scores of these items in Table 1, the cases were divided into three groups, that is a high, intermediate and low risk group, and the frequency of incidence of intraventricular hemorrhage was compared between each group in respect to treatment.

In the comparison of incidence of severe intraventricular hemorrhage in the high risk group, there was a significant difference namely 2 incidences in 10 treated cases (20%) and 5 incidences in 6 control cases (83.3%). The results are shown in Table 2.

TABLE 2

Incidence frequence of intraventricular hemorrhage in newborn infants treated with or without factor XIII concentrates

| | treated group | control group |
|---|---|---|
| high risk group | 3/10 (2/10) | 5/ 6 (5/ 6) |
| intermediate risk group | 0/ 5 (0/ 5) | 1/ 8 (1/ 8) |
| low risk group | 0/ 9 (0/ 9) | 1/10 (0/10) |
| total | 3/24 (2/24) | 7/24 (6/24) |

There was no incidence in 14 treated cases of intermediate and low risk groups.

Thus it was proved that the administration of factor XIII is effective for preventing intraventricular hemorrhage in premature infants including cases with high risk needing urgent treatment.

Process for Producing Factor XIII Concentrate

Factor XIII preparations are manufactured from human placenta or plasma by well-known methods. An example of the manufacturing methods using human placenta as raw material is as follows:

Freeze placentae and break them into fine pieces. Add an NaCl solution to the fine pieces of placentae, stir, and centrifuge to collect supernatant I. After ascertaining by enzyme immunoassay that this supernatant I is free from HBs antigen, add a Rivanol solution to it and collect precipitate II that contains factor XIII. After washing the precipitate, add an NaCl solution containing EDTA to it and stir. Remove undissolved substances (precipitate III) and obtain supernatant III. Then add an N-cetyl-pyridinium chloride solution to supernatant III to precipitate contaminating proteins and muco-polysaccharides. Add a Rivanol solution to the supernatant IV so obtained, and generate precipitate V that contains factor XIII. Add an NaCl solution containing EDTA to this precipitate V, stir, and remove undissolved substances (precipitate VI) to obtain supernatant VI. Add ammonium sulfate to supernatant VI to generate precipitate VII that contains factor XIII. Add an EDTA solution to precipitate VII and dialyze against a Tris-HCl buffer containing EDTA and sodium azide. After adjusting pH, remove precipitate VIII and have supernatant VIII undergo gel filtration to collect acive fractions. Add ammonium sulfate to the fractions and collect precipitate IX containing factor XIII. Dissolve this precipitate IX in a Tris-HCl buffer containing EDTA, dialyze against the same buffer, and adjust pH to collect a precipitate that contains factor XIII in the form of euglobulin. Dissolve the euglobulin precipitate in an NaCl solution containing EDTA, and add aminoacetic acid and sucrose. Then add ammonium sulfate to generate precipitate X containing factor XIII, and dissolve this precipitate X in an NaCl solution containing EDTA, and dialyze against the same solution. Adjust the titer of factor XIII using an NCl solution containing glucose and human serum albumin. Have this solution undergo sterile filtration, dispense into glass vials, and lyophilyze.

In addition to the above-mentioned fractionation method, factor XIII can also be manufactured by use of genetic engineering. Factor XIII preparations in accordance with this invention include all the factor XIII preparations manufactured by any possible method, including fractionation methods and genetic engineering methods.

Since factor XIII preparations manufactured by fractionation methods may possibly contain hepatitis virus, AIDS virus, etc., it is desired to inactivate these viruses by heat treatment or some other means. The heat treatment is performed as folows: dissolve the precipitate containing factor XIII in the form of euglobulin in an NaCl solution containing EDTA, and allow the solution to stand at approximately 60° C. for 10 hours or so. Amino acids (e.g., glycine), hydrocarbonates, etc. can be used as stabilizers during this incubation.

A lyophilized factor XIII preparation can directly be used as an injection by just dissolving it in distilled water for injection (JP), etc. before use. The concentration of factor XIII in the solution for injection should be about 250 units/4 ml. The injection can be given either intravenously or intramuscularly.

No change the factor XIII solution has been reported to be induced by mixture with other agents. It is generally considered, however, that administration of factor XIII mixed with other agents should be avoided.

Most desirably, factor XIII should be administered by injection, but possible dosage forms include parenteral ones such as micro-capsules and implants, oral ones such as liquids, tablets and capsules, and suppositories.

Dosage and Treatment Period

The daily dosage necessary to prevent intraventricular hemorrhage in premature infants is approximately 50–100 units.

Administration should be continued until the risks virtually disappear, i.e., for 3 days in usual cases. In cases where the risks increase, administration may be restarted at any time.

Example: Factor XIII, dispensed into vials by 250 units each and lyophilized, was dissolved in 4 ml of distilled water for injection (JP) to make a factor XIII injection.

We claim:

1. A method for the prevention of intraventricular hemorrhage in premature infants, which comprises administering to the said infants an effective amount of human coagulation factor XIII.

2. The method as claimed in claim 1, wherein the daily dosage is 50 to 100 units.

3. The method as claimed in claim 2, wherein the daily dosage is 70 to 100 units.

4. The method of claim 2, wherein the said dosage is applied for 3 days.

5. The method of claim 3, wherein the said dosage is applied for 3 days.

* * * * *